United States Patent [19]

Watanabe et al.

[11] Patent Number: 4,605,645
[45] Date of Patent: Aug. 12, 1986

[54] 5-FLUORO-2'-DEOXYURIDINE DERIVATIVES AND A PROCESS FOR THE PREPARATION THEREOF

[75] Inventors: Kenzo Watanabe; Yoshinori Kato, both of Hino; Masahiko Saito, Tokorozawa; Takeo Oba, Hino; Hisashi Fukushima; Takeshi Hara, both of Hachioji, all of Japan

[73] Assignee: Teijin Limited, Osaka, Japan

[21] Appl. No.: 448,087

[22] Filed: Dec. 9, 1982

[30] Foreign Application Priority Data

Dec. 9, 1981 [JP] Japan .................................. 56-196939
May 6, 1982 [JP] Japan .................................. 57-74478
Oct. 13, 1982 [JP] Japan .................................. 57-178507

[51] Int. Cl.$^4$ .................... C07H 15/12; C07H 17/00
[52] U.S. Cl. .................................. 514/51; 536/29
[58] Field of Search ................... 536/23, 29; 514/51

[56] References Cited

U.S. PATENT DOCUMENTS

| 4,247,544 | 1/1981 | Bergstrom et al. | 536/23 |
| 4,468,384 | 8/1984 | Bardos et al. | 536/29 |
| 4,472,386 | 9/1984 | Kodama et al. | 536/29 |

FOREIGN PATENT DOCUMENTS

| 2658672 | 6/1978 | Fed. Rep. of Germany | 536/23 |
| 3048877 | 7/1982 | Fed. Rep. of Germany | 536/29 |
| 56-113795 | 9/1981 | Japan . | |
| 0081386 | 6/1983 | Japan | 536/29 |
| 0093096 | 5/1984 | Japan | 536/29 |

OTHER PUBLICATIONS

DeClercq, Meth and Find Exptl Clin. Pharmacol., 2(5), 253-67 (1980).
Chemical Abstracts, 77:56546q (1972).
Chemical Abstracts, 89:135847q (1978).
Chemical Abstracts, 89:135848r (1978).
Chemical Abstracts, 68:13304f (1968).
Chemical Abstracts, 81:59867p (1974).
Chemical Abstracts, 91:83560k (1979).

*Primary Examiner*—Ethel G. Love
*Attorney, Agent, or Firm*—Sughrue, Mion, Zinn, Macpeak, and Seas

[57] ABSTRACT

5-fluoro-2'-deoxyuridine derivatives expressed by general formula (1) and their pharmacologically permissible salts

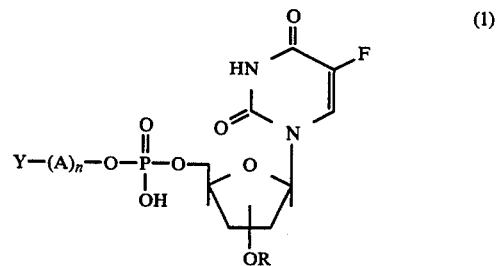

wherein A indicates a saturated or unsaturated divalent aliphatic hydrocarbon group having 1 to 30 carbon atoms; the letter n indicates 0 or 1, and when n is 0, it indicates that Y is directly bound to an oxygen atom; Y represents a hydrogen atom, phenyl group, or substituted phenyl group; however, when Y is a hydrogen atom, n is 1; R indicates a hydrogen atom or alcohol-protecting group.

These compounds have a very strong antitumor activity.

10 Claims, No Drawings

5-FLUORO-2'-DEOXYURIDINE DERIVATIVES AND A PROCESS FOR THE PREPARATION THEREOF

BACKGROUND OF THE INVENTION

This invention relates to 5-fluoro-2'-deoxyuridine derivatives and a process for the preparation thereof.

An antitumor substance 5-fluorouracil (5-FU) has the efficacy against a wide range of malignant tumor including brest cancer, gastric cancer, lung cancer, pancreatic cancer, hepatoma, uterine cancer, etc. when used singly or in combination with other drugs. However, with regard to the efficacy, side effects, pharmacokinetics, etc. of 5-FU, further improvement is wanted and intensive studies are actively conducted by many specialists in the medical circles. 5-FU is transformed intracellularly into 5-fluoro-2'-deoxyuridine-5'-phosphate, which inhibits thymidylate synthetase and this is generally known to be the major mechanism of its anticancer effect. 5-Fluoro-2'-deoxyuridine (5-FUdR) has a much stronger cytotoxic activity in vitro as compared with 5-FU, because it is more akin to active form than 5-FU. However, the activity of 5-FUdR in vivo is weak in spite of its strong activity in vitro. The improper pharmacokinetics of 5-FUdR may be the cause of the discrepancy between its activity in vitro and in vivo.

Various 5-FUdR derivatives have been prepared seeking for improved activities. For instance, 3-acyl-5-FUdR (Japanese Patent Laying-open No. 163586/79), 3',5'-diacyl-5-FUdR (Epitome of 100th anniversary lecture meeting of the Pharmacological Society of Japan, p.321, 1980), 5-FUdR whose 3-position and 3',5'-position are all acylated (Japanese Patent Laying-Open Nos. 113795/'81, 113796/'81, and 113797/'81) are known.

Also derivatives of 5-fluorouridine (5-FUR) having a phosphodiester bond at the 5'-position are known (Japanese Patent Laying-Open No. 29938/'78). However, even these derivatives are not satisfactory enough in view of their anticancer effects and side effects.

SUMMARY OF THE INVENTION

The object of the present invention is to provide 5-fluoro-2'-deoxyuridine derivatives which have a much stronger antitumor activity, are orally administrable, and show less side effects when compared with the known compounds mentioned above.

A further object of the present invention is to provide a process for the preparation of such 5-fluoro-2'-deoxyuridine derivatives.

5-Fluoro-2'-deoxyuridine derivatives that realize the object of the present invention are expressed by the following general formula (1):

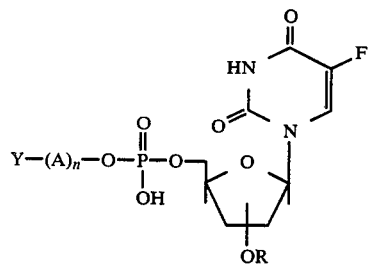

wherein A indicates a saturated or unsaturated divalent aliphatic hydrocarbon group having 1 to 30 carbon atoms; n indicates 0 or 1, and when n is 0, it indicates that Y is directly bound to an oxygen atom; Y represents hydrogen atom, phenyl group, or substituted phenyl group; however, when Y is hydrogen atom, n is 1; R indicates hydrogen atom or alcohol-protecting group.

For attaining the object of the present invention, 5-fluoro-2'-deoxyuridine derivatives expressed by the general formula (1) may also be prepared in the form of a salt so far as they are pharmacologically permissible.

DESCRIPTION OF THE PREFERRED EMBODIMENTS

In the aforementioned general formula (1), A indicates a saturated or unsaturated divalent aliphatic hydrocarbon group having 1 to 30, preferably 3 to 24, carbon atoms. The aliphatic hydrocarbon group may be either straight-chain or branched-chain. An unsaturated aliphatic hydrocarbon group is one having 1 to 5, preferably 1 to 3, double bonds or triple bonds at any positions in the molecule.

When Y in the general formula (1) is a hydrogen atom, the group Y—(A)$_n$— is expressed as H—A—, which represents a saturated or unsaturated monovalent aliphatic hydrocarbon group having 1 to 30 carbon atoms.

As examples of saturated aliphatic hydrocarbon group, for instance, a methyl group, ethyl group, propyl group, butyl group, pentyl group ($C_5$), hexyl group ($C_6$), heptyl group ($C_7$), octyl group ($C_8$), nonyl group ($C_9$), decyl group ($C_{10}$), undecyl group ($C_{11}$), dodecyl group ($C_{12}$), tridecyl group ($C_{13}$), tetradecyl group ($C_{14}$), pentadecyl group ($C_{15}$), hexadecyl group ($C_{16}$), heptadecyl group ($C_{17}$), octadecyl group ($C_{18}$), nonadecyl group ($C_{19}$) eicosyl group ($C_{20}$), heneicosyl group ($C_{21}$), docosyl group ($C_{22}$), tricosyl group ($C_{23}$), tetracosyl group ($C_{24}$), pentacosyl group ($C_{25}$), hexacosyl group ($C_{26}$), heptacosyl group, octacosyl group, nonacosyl group, triacontyl group, isopropyl group, isobutyl group, sec-butyl group, tert-butyl group, isopentyl group, 2-undecyl group, 2-methyl-2-undecyl group, 3-dodecyl group, 2-tetradecyl group, 2-methyl-2-tetradecyl group, 4-methyl-2-tetradecyl group, 2-pentadecyl group, 2-methyl-2-pentadecyl group, 2-methyl-3-hexadecyl group, 2-heptadecyl group, 2-methyl-2-heptadecyl group, 2-nonadecyl group, 2-methyl-2-nonadecyl group, 3-ethyl-3-eicosyl group, 2-heneicosyl group, 2-methyl-2-heneicosyl group, 2-tricosyl group, 2-methyl-2-tricosyl group, 4,6-dimethyl-2-tricosyl group, etc. may be mentioned but not be limited to them.

As examples of unsaturated aliphatic hydrocarbon group, for instance, an allyl group, 3-butenyl group, isobutenyl group, 2-hexenyl group, 3-hexenyl group, 4-octenyl group, 3-nonenyl group, 2-decenyl group, 2-dodecenyl group, 2-tridecenyl group, 4-tetradecenyl group, 4-pentadecenyl group, 2-hexadecenyl group, 9-hexadecenyl group, 9-heptadecenyl group, cis-6-octadecenyl group, cis-9-octadecenyl group, trans-11-octadecenyl group, 2-eicosenyl group, 2-triacontenyl group, geranyl group, 2,5-decadienyl group, 2,5,8-tetradecatrienyl group, linolyl group, linolenyl group, arachidonyl group, eicosapentaenyl group, propynyl group, 3-butynyl group, 3-pentynyl group, 4-octynyl group, 2-decynyl group, 3-tetradecynyl group, 3,5-tetradecadiynyl group, 3-octadecynyl group, 4-eicocynyl group, eicosapentaynyl group, tetradeca-3-en-6-ynyl group, and octadeca-3-en-6-ynyl group are mentioned. Of all these groups, aliphatic hydrocarbon groups having 10 to 24 carbon atoms are preferable.

When Y in the general formula (1) is a phenyl group, the group Y—$(A)_n$— is expressed as $C_6H_5$— or $C_6H_5$—A—, and as examples of the latter, a benzyl group, phenetyl group, 3-phenylpropyl group, 2-phenylpropyl group, 4-phenylbutyl group, 5-phenylpentyl group, 3-phenylpentyl group, 6-phenylhexyl group, 7-phenylheptyl group, 8-phenyloctyl group, 9-phenylnonyl group, 10-phenyldecyl group, 12-phenyl undecyl group, 14-phenyltetradecyl group, 16-phenylhexadecyl group, 20-phenyleicosyl group, cinnamyl group, 4-phenyl-3-butenyl group, 6-phenyl-2-hexenyl group, 5-phenyl-3-hexenyl group, 8-phenyl-3-octenyl group, 7-phenyl-3-octenyl group, 9-phenyl-3-nonenyl group, 10-phenyl-2-decenyl group, 14-phenyl-3-tetradecenyl group, 6-phenyl-2,4-hexadienyl group, 8-phenyl-3,6-octadienyl group, 11-phenyl-2,5,8-undecatrienyl group, 18-phenyl-2,6,10,14-octadecatetraenyl group, 3-phenyl-2-propynyl group, 4-phenyl-2-butynyl group, 6-phenyl-3-hexynyl group, 8-phenyl-3-octynyl group, 8-phenyl-5-octynyl group, 10-phenyl-2-decynyl group, 14-phenyl-3-tetradecynyl group, 18-phenyl-3-octadecynyl group, 6-phenyl-2,4-hexadiynyl group, 6-phenyl-hexa-2-en-4-ynyl group, 8-phenyl-2,5-octadiynyl group, 10-phenyl-deca-2,5-dien-8-ynyl group, and 14-phenyl-2,5,8-tetradecatriynyl group are mentioned.

When Y in the general formula (1) is a substitued phenyl group, this substituded phenyl group is one which has 1 to 5 substituent groups introduced to the phenyl group of aforementioned $C_6H_5$— or $C_6H_5$—A—. As substituent groups, a halogen atom, saturated or unsaturated aliphatic hydrocarbon group, wither straight-chained or branched, having 1 to 20 carbon atoms, acyl group and unsaturated acyl group, either straight-chained or branched, having 1 to 20 carbon atoms, alkyloxy group and unsaturated alkyloxy group, either stright-chained or branched, having 1 to 10 carbon atoms, acyloxy group or unsaturated acyloxy group, either stright-chained or branched, having 1 to 10 cabron atoms, etc. are mentioned. To give examples of substituent groups, a halogen atom such as fluorine, chlorine, bromine, iodine, etc.; alkyl groups such as methyl group, ethyl group, propyl group, isopropyl group, butyl group, tert-butyl group, pentyl group, 3-methylbutyl group, hexyl group, 2-hexyl group, heptyl group, 3-heptyl group, octyl group, nonyl group, decyl group, dodecyl group, tetradecyl group, octadecyl group, 8-ethyldecyl group, 3-butyl-tetradecyl group, etc.; unsaturated aliphatic hydrocarbon groups such as vinyl group, aryl group, 3-butenyl group, isopentenyl group, 3-hexenyl group, 4-decenyl group, 6-tetradecenyl group, 3-methyl-4-octenyl group, 7-ethyl-5-methyl-3-decenyl group, 2,4-hexadienyl group, ethynyl group, propargyl group, 3-butynyl group, 2-pentynyl group, 6-octynyl group, 5-decynyl group, 3,5-decadiynyl group, etc.; acyl groups such as formyl group, acetyl group, propanoyl group, butanoyl group, isobutanoyl group, pentanoyl group, pivaloyl, hexanoyl group, octanoyl group, 6-methylheptanoyl group, decanoyl group, tetradecanoyl group, octadecanoyl group, acryloyl group, 2-butenoyl group, 4-hexenoyl group, 5-decynoyl group, etc.; alkoxy groups such as methoxyl group, ethoxy group, propyloxy group, butoxy group, pentyloxy group, hexyloxy group, heptyloxy group, octyloxy group, decyloxy group, isopropoxy group, isobutoxy group, isoamyloxy group, 4-ethylhexyloxy group, 3-propylheptyloxy group, allyloxy group, 2-butenyloxy group, isopentenyloxy group, propargyloxy group, 3-octynyloxy group, etc.; and acyloxy groups such as formyloxy group, acetoxy group, propanoyloxy group, butanoyloxy group, isobutanoyloxy group, pentanoyloxy group, pivaloyloxy group, hexanoyloxy group, heptanoyloxy group, octanoyloxy group, nonanoyloxy group, decanoyloxy group, acryloyloxy group, 2-butenoyloxy group, 4-hexenoyloxy group, 5-decynoyloxy group, etc. may be mentioned. Preferable substituent groups are halogen, alkyl group having 1 to 8 carbon atoms, and acyl group having 1 to 8 carbon atoms.

In case where Y in the general formula (1) is a phenyl group or substituted phenyl group, it is desirable that A is a saturated or unsaturated aliphatic hydrocarbon group having 3 to 8 carbon atoms or that n=0, that is the phenyl group or substituted phenyl group is bound directly to an oxygen atom.

In the general formula (1), R indicates hydrogen atom or alcohol-protecting group. As alcohol-protecting groups, for instance, acyl groups such as formyl group, acetyl group, propanoyl group, butanoyl group, isobutanoyl group, pentanoyl group, hexanoyl group, octanoyl group, decanoyl group, tetradecanoyl group, octadecanoyl group, benzoyl group, toluoyl group, p-chlorobenzoyl group, etc. and ether groups such as a tetrahydropyranyl group, tetrahydrofuryl group, 2,2,2-trichloroethyl group, methoxymethyl group, 1-ethoxyethyl group, 4-methoxy-4-pyranyl group, trimethylsilyl group, dimethyl-tert-butylsilyl group, tert-butyl-diphenylsilyl group, etc. may be mentioned. A hydrogen atom or an acyl group having 1 to 10 carbon atoms is preferable as R.

A 5-fluoro-2'-deoxyuridine derivative of the present invention expressed by aforementioned general formula (1) is obtained by allowing 3'-substituted-5-fluoro-2'-deoxyuridine expressed by the following general formula (2)

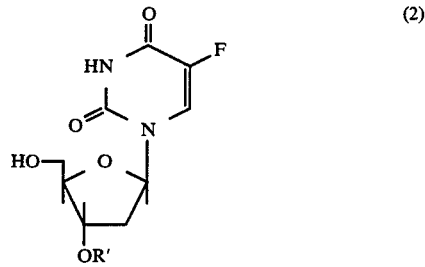

(wherein R' indicates an alcohol-protecting group,) to react with a phosphate monoester expressed by general formula (3)

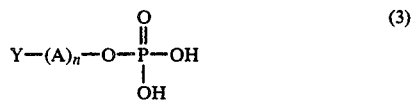

(wherein definitions of A, n, and Y are as same as those given in case of general formula (1)) in the presence of a condensing agent, followed by the removal of a protecting group as case may require.

3'-Protected-5-fluoro-2'-deoxyuridine expressed by the abovementioned general formula (2) to be used in the present invention may be prepared according to any method; however, to give an example, J. A. Montgomery et al. propose a method in which 3'-protected-5-fluoro-2'-deoxyuridine is synthesized from 2'-deoxy-5-fluorouridine through three steps of procedure (Journal of Medical and Pharmaceutical Chemistry, 5, 24, (1962)).

A phosphate monoester expressed by the above-mentioned general formula (3) to be used in the present invention is obtained, for instance, by condensing excess phosphorous oxychloride and an alcohol into monoalkylphosphoryl chloride, followed by hydrolysis (Synthesis, 704, (1974)).

The condensation reaction between aforementioned compound of general formula (2) and aforementioned compound of general formula (3) is conducted with the use of a condensing agent in an organic solvent. As the condensing agent, it is desirable to use such coarbodiimide as dicyclohexyl carbodiimide, etc.; such arylsulfonyl chloride as 2,4,6-triisopropylbenzenesulfonyl chloride, benzenesulfonyl chloride, p-toluenesulfonyl chloride, 2,4,6-trimethylbenzenesulfonyl chloride, 8-quinolinesulfonyl chloride, etc.; and such arylsulfonamide as 2,4,6-trimethylbenzenesulfonyl imidazolide, 2,4,6-triisopropylbenzenesulfonyl imidazolide, 2,4,6-trimethylbenzensulfonyl triazolide, 2,4,6-triisopropylbenzenesulfonyl triazolide, 2,4,6-trimethylbenzenesufonyl-3-nitrotriazolide, 2,4,6-triisopropylbenzenesulfonyl-3-nitrotriazolide, etc. As for the reaction solvent, it is desirable to use an aprotic organic solvent which has enough solvency and does not retard the process of the reaction. In order to obtain the best result, the selection of solvent must be made taking the reaction substrate and the condensing agent into consideration. However, generally speaking, pyridine, N,N-dimethylformamide, N,N-dimethylacetamide, dimethyl sulfoxide, hexamethyl phosphorus triamide, ethyl acetate, tetrahydrofuran, 1,2-dimethoxyethane, dioxane, chloroform, methylene chloride, etc. can be used singly or mixedly. Also, in this condensation reaction, organic bases such as triethylamine, pyridine, γ-dimethylaminopyridine, N,N-dimethylaniline, tributylamine, etc., for instance, are used as auxiliary agent of the condensation reaction in some cases.

The reaction time required for the condensation reaction varies depending upon the substrate, condensing agent, and solvent; however, the reaction is usually completed within about 1 hour to 4 days. The reaction temperature is usually in the range of $-30°$ C. to $100°$ C. and it is desirable to carry out the reaction at $0°$ C. to room temperature. However, in case where the chemical reactivity of the reaction mixture is low, the reaction may be conducted by heating.

After the condensation reaction is completed the protecting group R' may be removed if necessary. Since acyl groups such as an acetyl group, benzoyl group, etc. are deemed to be removed in vivo, they may not necessarily be removed; however, in case of ether groups, it is preferable to remove them. The methods for eliminating a protecting group differ depending upon the kind of the protecting group; however, in case of an acyl group, for instance, it can be removed easily when it is treated with ammonia/methanol, potassium carbonate/methanol-water, triethylamine/methanol-water, etc. In the case of ether groups, they are also removed by commonly used methods in organic synthesis. For example, they may be removed by treating one of the following conditions; aqueous acetic acid, conc. $H_2SO_4$ aqueous acetic acid, HCl/methanol, HCl/tetrahydrofuran, p-toluenesulfonic acid/methanol, Zn/acetic acid, $n-Bu_4N+F-$/tetrahydrofuran, aqueous HF/acetonitril, $BF_3.OEt_2$/-chloroform, etc.

Thus obtained 5-fluoro-2'-deoxyuridine derivatives can be isolated by appropriate selection and combination of ordinary procedures of extraction, column chromatography on silica gel, ion-exchange column chromatography, high performance liquid chromatography (HPLC), recrystallization, etc.

If desired, the obtained 5-fluoro-2'-deoxyuridine derivatives may be changed into the form of a pharmacologically permissible salt according to a known method. As the salt of 5-fluoro-2'-deoxyuridine derivatives, such ammonium salts as an ammonia salt, morpholine salt, pyrrolidine salt, piperidine salt, pyridine salt, and triethylamine salt; such alkali metal salts as sodium, potassium, and lithium; such alkaline earth metal salts as calcium, magnesium, and barium; and such transition metal salts as copper, zinc, silver, and aluminium, for instance, may be mentioned.

5-Fluoro-2'-deoxyuridine derivatives and their pharmacologically permissible salts proposed in the present invention are novel compounds never referred to in any documents and display strong antitumor activities when administered orally.

The following Examples illustrate the present invention in detail:

EXAMPLE 1

Preparation of
5-fluoro-2'deoxyuridine-5'-docosylphosphate (Y=H, A=—$(CH_2)_{22}$—, R=H)

1.9 g (4.5 mmole) of docosylphosphate ($C_{22}$) and 864 mg (3 mmole) of 3'-acetyl-5-fluoro-2'-deoxyuridine were dissolved in 80 ml of anhydrous pyridine. 1.72 g (9 mmole) of p-toluenesulfonyl chloride was added to the solution with stirring while cooling with ice and the solution was kept stirring overnight at room temperature. Then 3 ml of water was added thereto, stirred for 30 minutes, and the solvent was removed by distillation under reduced pressure.

The crude product obtained in the above condensation reaction was stirred overnight in a mixture of 20 ml of concentrated aqueous ammonia and 40 ml of methanol at room temperature. The solvent was distilled away from the reaction mixture under diminished pressure. Water and aqueous solution of 2 normal sodium hydroxide were added to the residue to obtain a pH value of about 12 and was then washed with butanol. 2 normal hydrochloric acid was added to its aqueous layer while cooling with ice to lower the pH to about 2 and the deposited precipitate was separated by centrifugation. Thus obtained powder was dissolved in a small amount of butanol and the solution was injected into a column chromatography on silica gel. The eluates from butanol-acetic acid-water (20:1:1) to (10:1:1) were collected and pooled and concentrated to give a powder. The obtained powder was washed with a small amount of methanol to give 485 mg of 5-fluoro-2'-deoxyuridine-5'-docosylphosphate. The yield was 23%.

IR(KBr): 3490, 2940, 2860, 1710, 1265, 1210, 1130, 1070, 1040 $cm^{-1}$.

UV: λman 268 nm

NMR($\delta_{CDCl_3-C_3COD}^{TMS}$): 0.89 (br.t, 3H), 1.0~2.0 (m, 40H), 2.0~2.5 (m, 2H), 3.9~4.7 (m, 6H), 6.28 (br.t, 31H), 7.90 (d.1H, J=6.5 Hz)

EXAMPLE 2

Preparation of
5-fluoro-2'-deoxyuridine-5'-octadecylphosphate (Y=H, A=—(CH$_2$)$_{18}$—, R=H)

1.35 g (3.7 mmole) of octadecylphosphate (C$_{18}$) and 881 mg (2.06 mmole) of 3'-acetyl-5-fluoro-2'-deoxyuridine were dissolved in 50 ml of anhydrous pyridine, and 0.86 g (6.6 mmole) of p-toluenesulfonyl chloride was added thereto with stirring while cooling with ice. The mixture was kept stirring at room temperature overnight.

The reaction mixture was thereafter subjected to the same process as Example 1 to obtain 920 mg of 5-fluoro-2'-deoxyuridine-5'-octadecylphosphate. The yield was 51%.

Melting point: 121°~124° C.
IR(KBr): 3480, 2940, 2855, 1705, 1268, 1210, 1130, 1060, 1040 cm$^{-1}$.
UV: λmax 268 nm
NMR($\delta_{CDCl_3-D_3COD}^{TMS}$) 0.88 (br.t, 3H), 0.9~2.0 (m, 32H), 2.0~2.5 (m, 2H), 3.8~4.7 (m, 6H), 6.36 (br.t, 1H), 7.98 (d,1H, J=6 Hz)

EXAMPLE 3

Preparation of
5-fluoro-2'-deoxyuridine-5'-tetradecylphosphate
(Y=H, A=—(CH$_2$)$_{14}$—, R=H)

1.39 g (4.5 mmole) of tetradecylphosphate and 864 mg (3.0 mmole) of 3'-acetyl-5-fluoro-2'-deoxyuridine were dissolved in 50 ml of anhydrous pyridine. 3.0 g (15.7 mmole) of p-toluenesulfonyl chloride was added to the solution with stirring while cooling with ice and stirred at room temperature for 2 days. The mixture was again cooled with ice and 3 ml of water was added to the mixture. After the mixture was agitated for 30 minutes, the solvent was removed by distillation under reduced pressure. The obtained crude product of the condensation reaction was stirred overnight in a mixture of 20 ml of concentrated aqueous ammonia and 40 ml of methanol at room temperature. The solvent was removed from the reaction mixture by distillation under reduced pressure. Water and aqueous solution of 2 normal sodium hydrooxide were added to the residue to obtain a pH of about 12. This was washed with butanol. 2 normal hydrochloric acid was added to its aqueous layer while cooling with ice to lower the pH to about 2. The desired substance was extracted from the solution by use of butanol. The butanol layer was washed with water and then concentrated under reduced pressure. The obtained residue was dissolved in a small amount of butanol and chromatographic separation was carried out on a column of silica gel. The eluates from butanol-acetic acid-water (20:1:1) to (7:1:1) were pooled and the solvent was removed therefrom by distillation. The residue was dissolved in a small amount of methanol and the insoluble substances were removed by filtration. The filtered solution was let fall dropwise into 400 ml of ether and the deposited precipitate was collected by centrifugation to obtain 843 mg of 5-fluoro-2'-deoxyuridine-5'-tetradecylphosphate. The yield was 48%.

The product obtained in the above was further purified by high performance liquid chromatography (HPLC) (instruments, Waters LTD S-500; column, λ Bondapack C-18; solvent, CH$_3$CN—H$_2$O—AcOH (59:39:2)) and was then recrystallized from a mixture of acetonitrile-water-acetic acid (20:10:1). The refined product thus obtained had the following physical properties:

Melting point: 125° to 126° C.
IR(KBr): 3490, 2950, 2875, 1716, 1692, 1660, 1268, 1218, 1132, 1060, 1040 cm$^{-1}$.
UV: λmax 268 nm
Elemental analysis: Calculated data: C=52.86; H=7.72; N=5.36. Found values: C=53.0; H=8.1; N=5.1.
NMR($\delta_{COCl_3-D_3COD}^{TMS}$) 0.8~1.9 (m, 27H), 2.1~2.4 (m, 2H), 3.8~4.6 (m, 6H), 6.19 (br.t, 1H), 7.89 (d,1H, J=7 Hz)

EXAMPLE 4

Preparation of
5-fluoro-2'-deoxyuridine-5'-decylphosphate (Y=H, A=—(CH$_2$)$_{10}$—, R=H)

1.43 g (6 mmole) of decylphosphate and 1.15 g (4 mmole) of 3'-acetyl-5-fluoro-2'-deoxyuridine were dissolved in 60 ml of anhydrous pyridine, to which 2.3 g (12 mmole) of p-toluenesulfonyl chloride was added with stirring while cooling with ice. The mixture was stirred overnight at room temperature.

After that, the reaction mixture was processed according to Example 3 but without HPLC purification and 1.1 g of 5-fluoro-2'-deoxyuridine-5'-decylphosphate was obtained. The yield was 59%.

IR(KBr): 3490, 2940, 2860, 1710, 1270, 1218, 1124, 1060, 1040 cm$^{-1}$.
UV: λmax 268 nm
NMR($\delta_{CDCl_3-D_3COD}^{TMS}$): 0.89 (br.t, 3H), 0.9~1.9 (m, 16H), 2.0~2.5 (m, 2H), 3.8~4.7 (m, 6H), 6.28 (br.t, 1H), 7.89 (d, 1H, J=6.5 Hz)

EXAMPLE 5

Preparation of
5-fluoro-2!-deoxyuridine-5'-tetracosylphosphate (Y=H, A=-(CH$_2$)$_{24}$-, R=H)

697 mg (1.5 mmole) of tetracosylphosphate and 288 mg (1.0 mmole) of 3'-acetyl-5-fluoro-2'-deoxyuridine were dissolved in 30 ml of anhydrous pyridine. 573 mg (3.0 mmole) of p-toluenesulfonyl chloride was added to the solution with stirring while cooling with ice and the mixture was stirred overnight at room temperature.

Thereafter, the reaction mixture was treated according to Example 1 to obtain 83 mg of 5-fluoro-2'-deoxyuridine-5'-tetracosylphosphate powder. The yield was 12%.

IR(KBr): 3490, 2945, 2860, 1706, 1664, 1268, 1212, 1130, 1050 cm$^{-1}$.
UV: λmax 266 nm
NMR($\delta_{CDCl_3-COD}^{TMS}$): 0.89 (br.t, 3H), 0.9~2.0 (m, 44H), 2.0~2.5 (m, 2H), 3.8~4.6 (m, 6H), 6.30 (br.t, 1H), 7.91 (d, 1H, J=6.5 Hz)

EXAMPLE 6

Preparation of
5-fluoro-2'-deoxyuridine-5'-eicosylphosphate (Y=H, A=-(CH$_2$)$_{20}$-, R=H)

1.77 g (4.5 mmole) of eicosylphosphate (C$_{20}$) and 864 mg (3.0 mmole) of 3'-acetyl-5-fluoro-2'-deoxyuridine were dissolved in 80 ml of anhydrous pyridine. 1.72 g (9 mmole) of p-toluenesulfonyl chloride was added thereto with stirring while cooling with ice and the mixture was stirred overnight at room temperature.

Thereafter, the reaction mixture was processed according to Example 1 to obtain 1.06 g of 5-fluoro-2'-deoxyuridine-5'-eicosylphosphate. The yield was 57%.

IR(KBr): 3490, 2950, 2875, 1710, 1264, 1212, 1135, 1062, 1040 cm$^{-1}$.

UV: λmax 267 nm

NMR($\delta_{CDCl_3\text{-}D_3COD}^{TMX}$): 0.90 (br.t, 3H), 0.9~1.9 (m, 36H), 2.0~2.5 (m, 2H), 3.8~4.6 (m, 6H), 6.33 (br.t, 1H), 7.95 (d,1H, J=7 Hz)

EXAMPLE 7

Preparation of
5-fluoro-2'-deoxyuridine-5'-dodecylphosphate (Y=H, A=—(CH$_2$)$_{12}$—, R=H)

1.2 g (4.5 mmole) of dodecylphosphate (C$_{12}$) and 864 mg (3.0 mmole) of 3'-acetyl-5-fluoro-2'-deoxyuridine were dissolved in 80 ml of anhydrous pyridine. 1.72 g (9 mmole) of p-toluensulfonyl chloride was added to the solution with stirring while cooling with ice and the mixture was kept stirring overnight at room temperature.

After that, the reaction mixture was treated in the same way as Example 3 but without HPLC purification to give 870 mg of 5-fluoro-2'-deoxyuridine-5'-dodecylphosphate. The yield was 59%.

Melting point: 109°~114° C.

IR(KBr): 3495, 2950, 2875, 1710, 1668, 1270, 1218, 1138, 1060, 1040 cm$^{-1}$.

UV: λmax 268 nm

NMR($\delta_{CDCl_3\text{-}D_3COD}^{TMS}$): 0.89 (br.t, 3H), 0.9~1.9 (m, 20H), 2.0~2.5 (m, 2H), 3.8~4.6 (m, 6H), 6.29 (br.t, 1H), 7.90 (d, 1H, J=6.5 Hz)

EXAMPLE 8

Preparation of
5-fluoro-2'-deoxyuridine-5'-hexadecylphosphate
(Y=H, A=—(CH$_2$)$_{16}$—, R=H)

1.52 g (4.5 mmole) of hexadecylphosphate (C$_{16}$) and 864 mg (3.0 mmole) of 3'-acetyl-5-fluoro-2'-deoxyuridine were dissolved in 80 ml of anhydrous pyridine, to which solution 1.72 g (9 mmole) of p-toluenesulfonyl chloride was added with stirring while cooling with ice. The mixture was then kept stirring overnight at room temperature.

The reaction mixture was thereafter treated according to Example 3 but without HPLC purification to give 795 mg of 5-fluoro-2'-deoxyuridine-5'-hexadecylphosphate. The yield was 47%.

Melting point: 121°~124° C.

IR(KBr): 3490, 2945, 2870, 1705, 1268, 1220, 1138, 1062, 1040 cm$^{-1}$.

UV: λmax 268 nm

NMR($\delta_{CDCl_3\text{-}D_3COD}^{TMS}$): 0.90 (br.t, 3H), 1.0~1.9 (m, 28H), 2.0~2.5 (m, 2H), 3.8~4.6 (m, 6H), 6.26 (br.t, 1H), 7.89 (d, 1H, J=6.5 Hz)

EXAMPLE 9

Preparation of
3'-acetyl-5-fluoro-2'-deoxyuridine-5'-decylphosphate
(Y=H, A=—(CH$_2$)$_{10}$—, R=—COCH$_3$)

1.07 g (4.5 mmole) of decylphosphate (C$_{10}$) and 864 mg (3.0 mmole) of 3'-acetyl-5-fluoro-2'-deoxyuridine were dissolved in 80 ml of anhydrous pyridine. 1.3 g (6.82 mmole) of p-toluenesulfonyl chloride was added to the solution with stirring while cooling with ice and the mixture was stirred overnight at room temperature. 10 ml of water was added thereto, stirred for 30 minutes, and the solvent was removed by distillation under diminished pressure. About 200 ml of butanol and about 200 ml of water were added to the residue to have the desired substance extracted with butanol. The butanol layer were purified by washing with water two times. Then butanol was removed from the butanol layer by distillation under reduced pressure. The obtained residue was dissolved in a small amount of butanol and the solution was subjected to a column chromatography on sillica gel. The eluates from butanol-acetic acid-water (10:1:1) were collected. The solvent was distilled away from the pooled eluate. Extraction and purification were again carried out for the obtained residue with the use of butanol and water in the same way as the above. Butanol was removed from the butanol layer by distillation under reduced pressure. Thus obtained residue was dissolved in a small amount of butanol and insoluble substances were eliminated by filtration. The filtrate was let fall in drops into ether and a precipitate was collected by centrifugation to give 865 mg of 3'-acetyl-5-fluoro-2'-deoxyuridine-5'-decylphosphate. The yield was 57%.

IR(KBr): 2945, 2860, 1720, 1240, 1198, 1110, 1060 cm$^{-1}$.

UV: λmax 267 nm

NMR($\delta_{CDCl_3}^{TMS}$): after CH$_2$N$_2$ treatment*: 0.87 (br.t, 3H), 1.0~2.0 (m, 16H), 2.05 (s, 3H), 2.0~2.5 (m, 2H), 3.31 (s, 3H), 3.74 (d, 3H, J=11 Hz), 3.8~4.4 (m, 5H), 5.1~5.35 (m, 1H), 6.28 (br.t, 1H), 7.68 (d, 1H, J=6 Hz)

* The 3-position and phosphoric acid part are both methylated.

EXAMPLE 10

Preparation of
3'-acetyl-5-fluoro-2'-deoxyuridine-5'-dodecylphosphate
(Y=H, A=—(CH$_2$)$_{12}$—, R=—COCH$_3$)

1.20 g (4.5 mmole) of dodecylphosphate (C$_{12}$) and 864 mg (3.0 mmole) of 3'-acetyl-5-fluoro-2'-deoxyuridine were dissolved in 80 ml of anhydrous pyridine. 1.3 g (6.82 mmole) of p-toluenesulfonyl chloride was added thereto with stirring while cooling with ice and the mixture was stirred overnight at room temperature.

The reaction mixture was thereafter treated according to Example 9 to give 660 mg of 3'-acetyl-5-fluoro-2'-deoxyuridine-5'-dodecylphosphate. The yield was 41%.

IR(KBr): 2940, 2860, 1720, 1238, 1200, 1105, 1060 cm$^{-1}$.

UV: λmax 267 nm

NMR($\delta_{CDCl_3}^{TMS}$) after CH$_2$N$_2$ treatment: 0.88 (br.t, 3H), 1.0~2.0 (m, 20H), 2.06 (s, 3H), 2.0~2.5 (m, 2H), 3.30 (s, 3H), 3.73 (d, 3H, J=11 Hz), 3.8~4.4 (m, 5H), 5.1~5.35 (m, 1H), 6.30 (br.t, 1H), 7.69 (d, 1H, J=6 Hz)

EXAMPLE 11

Preparation of
3'-acetyl-5-fluoro-2'-deoxyuridine-5'-tetradecylphosphate (Y=H, A=—(CH$_2$)$_{14}$—, R=—COCH$_3$)

1.45 g (4.5 mmole) of tetradecylphosphate (C$_{14}$) and 864 mg (3.0 mmole) of 3'-acetyl-5-fluoro-2'-deoxyuridine were dissolved in 80 ml of anhydrous pyridine. 1.3 g (6.82 mmole) of p-toluenesufonyl chloride was added to the solution with stirring while cooling with ice and the mixture was stirred overnight at room temperature.

After that, the reaction mixture was treated according to Example 9 to obtain 500 mg of 3'-acetyl-5-fluoro-2'-deoxyuridine-5'-tetradecylphosphate. The yield was 29%.

Melting point: 206°~207° C.

IR(KBr): 2955, 2880, 1728, 1712, 1680 (sh), 1242, 1198, 1120, 1070 cm$^{-1}$.

UV: λmax 268 nm

NMR($\delta_{CDCl_3}{}^{TMS}$): 0.88 (br.t, 3H), 1.0~1.9 (m, 24H), 2.04 (s, 3H), 2.15~2.5 (m, 2H), 3.75~4.45 (m, 5H), 5.1~5.45 (m, 1H), 6.1~6.45 (m, 1H), 7.87 (d, 1H, J=7 Hz)

EXAMPLE 12

Preparation of 3'-acetyl-5-fluoro-2'-deoxyuridine-5'-hexadecylphosphate (Y=H, A=—(CH$_2$)$_{16}$—, R=—COCH$_3$)

1.45 g (4.5 mmole) of hexadecylphosphate (C$_{16}$) and 864 mg (3.0 mmole) of 3'-acetyl-5-fluoro-2'-deoxyuridine were dissolved in 80 ml of anhydrous pyridine, and 1.3 g (6.82 mmole) of p-toluensulfonyl chloride was added thereto with stirring while cooling with ice. The mixture was stirred overnight at room temperature.

The reaction mixture was thereafter treated according to Example 9 to give 559 mg of 3'-acetyl- 5-fluoro-2'-deoxyuridine-5'-hexadecylphosphate. The yield was 32%.

Melting point: 195°~199° C.

IR(KBr): 2940, 2860, 1718, 1235, 1200, 1112, 1062 cm$^{-1}$.

UV: λmax 267 nm

NMR($\delta_{CDCl_3}{}^{TMS}$) after CH$_2$N$_2$ treatment: 0.89 (br.t, 3H), 1.0~2.0 (m, 28H), 2.05 (s, 3H), 2.0~2.5 (m, 2H), 3.32 (s, 3H), 3.74 (d, 1H, J=11 Hz), 3.8~4.4 (m, 5H), 5.1~5.35 (m, 1H), 6.29 (br.t, 1H), 7.69 (d, 1H, J=6.5 Hz)

EXAMPLE 13

Preparation of 3'-acetyl-5-fluoro-2'-deoxyuridine-5'-octadecylphosphate (Y=H, A=—(CH$_2$)$_{18}$—, R=—COCH$_3$)

1.65 g (4.5 mmole) of octadecyphosphate (C$_{18}$) and mg (3.0 mmole) of 3'-acetyl-5-fluoro-2'-deoxyuridine were dissolved in 80 ml of anhydrous pyridine and 1.3 g (6.82 mmole) of p-toluenesufonyl chloride was added thereto with stirring while cooling with ice. The mixture was stirred overnight at room temperature.

The reaction mixture was thereafter treated according to Example 9 to obtain 1.60 g of 3'-acetyl-5-fluoro-2'-deoxyuridine-5'-octadecylphosphate. The yield was 84%.

Melting point: 198°~202° C.

IR(KBr): 2940, 2860, 1710, 1235, 1200, 1110, 1060 cm$^{-1}$.

UV: λmax 267 nm

NMR($\delta_{CDCl_3}{}^{TMS}$) after CH$_2$N$_2$ treatment: 0.89 (br.t, 3H), 1.0~2.0 (m, 32H), 2.05 (s, 3H), 2.0~2.5 (m, 2H), 3.30 (s, 3H) 3.75 (d, 3H, J=11 Hz), 3.8~4.4 (m, 5H), 5.1~5.35 (m, 1H), 6.30 (br.t, 1H), 7.68 (d, 1H, J=6.5 Hz)

EXAMPLE 14

Preparation of 3'-acetyl-5-fluoro-2'-deoxyuridine-5'-eicosylphosphate (Y=H, A=—(CH$_2$)$_{20}$—, R=—COCH$_3$)

1.18 g (3.0 mmole) of eicosylphosphate (C$_{20}$) and mg (2.0 mmole) of 3'-acetyl-5-fluoro-2'-deoxyuridine were dissolved in 60 ml of anhydrous pyridine. 1.14 g (5.98 mmole) of p-toluenesulfonyl chloride was added to the solution with stirring while cooling with ice and the mixture was stirred overnight at room temperature.

After that, the reaction mixture was treated according to Example 9 to give 770 mg of 3'-acetyl-5-fluoro-2'-deoxyuridine-5'-eicosylphosphate. The yield was 58%.

Melting point: 187°~193° C.

IR(KBr): 2945, 2860, 1720, 1700, 1240, 1200, 1120, 1070 cm$^{-1}$.

UV: λmax 267 nm

NMR ($\delta_{CDCl_3}{}^{TMS}$) after CH$_2$N$_2$ treatment: 0.89 (br.t, 3H), 1.0~2.0 (m, 36H), 2.05 (s, 3H), 2.0~2.5 (m, 2H), 3.31 (s, 3H), 3.76 (d, 3H, J=11 Hz), 3.8~4.4 (m, 5H), 5.1~5.35 (m, 1H), 6.27 (br.t, 1H), 7.68 (d, 1H, J=6.5 Hz)

EXAMPLE 15

Preparation of 3'-acetyl-5-fluoro-2'-deoxyuridine-5'-(9-cis-octadecenyl)phosphate (Y=H, A=—(CH$_2$)$_8$—CH$\overset{c}{=}$CH(CH$_2$)$_8$—, R=—COCH$_3$)

1.89 g (5.2 mmole) of 9-cis-octadecenyl phosphate and 1.15 g (4.0 mmole) of 3'-acetyl-5-fluoro-2'-deoxyuridine were dissolved in 80 ml of anhydrous pyridine. 2.3 g (12.1 mmole) of p-toluenesulfonyl chlorid was added to the solution with stirring at room temperature and the mixture was kept stirring overnight.

The reaction mixture was thereafter treated according to Example 9 to obtain 982 mg of 3'-acetyl-5-fluoro-2'-deoxyuridine-5'-(9-cis-octadecenyl) phosphate. The yield was 39%.

IR(KBr): 2950, 2870, 1710, 1240, 1108, 1068 cm$^{-1}$.

UV: λmax 267 nm

NMR ($\delta_{CDCl_3}{}^{TMS}$): 0.88 (br. t, 3H), 1.0~2.5 (n, 30H), 2.03 (s, 3H), 3.8~4.4 (m, 5H), 5.26 (br.t, 2H, J=4.5 Hz, +1H), 6.22 (br.t, 1H, J=6 Hz), 7.88 (d, 1H, J=7 Hz)

EXAMPLE 16

Preparation of 5-fluoro-2'-deoxyuridine-5'-(9-cis-octadecenyl)phosphate (Y=H, A=—(CH$_2$)$_8$CH$\overset{c}{=}$CH(CH$_2$)$_8$—, R=H)

500 mg (0.789 mmole) of 3'-acetyl-5-fluoro-2'-deoxyuridine-5'-(9-cis-octadecenyl)phosphate prepared in Example 15 was dissolved in a mixed solvent consisting bf 10 ml of methanol and 5 ml of 30% aqueous ammonia and the solution was stirred overnight at room temperature. The solvents and ammonia were removed by distillation under reduced pressure. The residue was dissolved in butanol. The butanol layer was washed with water twice and then concentrated. The concentrate was dissolved in a small amount of butanol. The solution thus obtained was let fall dropwise in ether and the powdery precipitate was collected by centrifugation to give 370 mg of 5-fluoro-2'-deoxyuridine-5'-(9-cis-octadecenyl)phosphate. The yield was 80%.

IR(KBr): 3460, 2950, 2880, 1705, 1266, 1200 cm$^{-1}$.

UV: $\lambda_{max}{}^{MeoH}$ 266 nm

NMR($\delta_{CDCl_3}{}^{TMS}$) after CH$_2$N$_2$ treatment: 0.86 (br.t, 3H), 1.0~2.6 (m, 30H), 3.30 (s, 3H, N-Me), 3,74 (d, 3H, J=11 Hz), 3,7~4.6 (m, 6H), 5.26 (br.t, 2H, J=4.5 Hz), 6.23 (br.t, 1H, J=6 Hz), 7.65 (d, 1H, J=6.5 Hz)

EXAMPLE 17

Preparation of 3′-acetyl-5-fluoro-2′-deoxyuridine-5′-linolylphosphate (Y=H, A=—(CH₂)₅CH≝CHCH₂CH≝CH (CH₂)₈—, R=—COCH₃)

2.0 g (5.8 mmole) of linolylphosphate and 1.1 g (3.9 mmole) of 3′-acetyl-5-fluorouridine were dissolved in 20 ml of anhydrous pyridine. 3.0 g (15.6 mmole) of p-toluenesulfonyl chloride was added to the solution with stirring while cooling with ice and the mixture was stirred overnight at room temperature.

The reaction mixture was thereafter treated according to Example 9 to obtain 1.33 g of powdery 3′-acetyl-5-fluoro-2′-deoxyuridine-5′-linolylphosphate. The yield was 55%.

IR(KBr): 2950, 2875, 1710, 1240, 1110, 1060 cm⁻¹.
UV: $\lambda_{max}^{MeOH}$ 267 nm
NMR($\delta_{CDCl_3}^{TMS}$) after CH₂N₂ treatment: 0.88 (br.t, 3H), 1.0~2.8 (m, 26H), 2.06 (s, 3H), 3.28 (s, 3H, N-Me), 3.72 (d, 3H, J=11 Hz, OMe), 3.7~4.6 (m, 5H), 5.25 (br.t, 4H, +1H), 6.20 (br.t, 1H, J=6 Hz), 7.67 (d, 1H, J=6 Hz)

EXAMPLE 18

Preparation of 5-fluoro-2′-deoxyuridine-5′-linolylphosphate (Y=H, A=—(CH₂)₅CH≝CHCH₂CH≝CH(CH₂)₈—, R=H)

1.1 g (1.8 mmole) of 3′-acetyl-5-fluoro-2′-deoxyuridine-5′-linolylphosphate prepared in Example 17 was treated in the same way as Example 16 to obtain 0.88 g of 5-fluoro-2′-deoxyuridine-5′-linolylphosphate. The yield was 83%.

IR(neat): 3490, 2950, 2875, 1705, 1265, 1050 cm⁻¹.
UV: $\lambda_{max}^{MeOH}$ 268 nm
NMR($\delta_{CDCl_3}^{TMS}$) after CH₂N₂ treatment: 0.87 (br.t, 3H), 1.0~2.8 (m, 26H), 3.29 (s, 3H, N-Me), 3.73 (d, 3H, J=11 Hz, OMe), 3.7~4.6 (m, 6H), 5.26 (br.t, 4H), 6.21 (br.t, 1H, J=6 Hz), 7.62 (d, 1H, J=6 Hz)

EXAMPLE 19

Preparation of 3′-acetyl-5-fluoro-2′-deoxyuridine-5′-linolenylphosphate (Y=H, A=—(CH₂)₂CH≝CHCH₂CH≝CH CH₂CH≝CH(CH₂)₈—, R=COCH₃

2.7 g (7.5 mmole) of linolenylphosphate and 1.44 g (5.0 mmole) of 3′-acetyl-5-fluorouridine were dissolved in 80 ml of anhydrous pyridine. 2.86 g (15.0 mmole) of p-toluenesufonyl chloride was added to the solution with stirring at room temperature and the mixture was stirred overnight.

The reaction mixture was thereafter treated in the same way as Example 9 to obtain 1.36g of 3′-acetyl-5-fluoro-2′-deoxyuridine-5′-linolenylphosphate. The yield was 43%.

IR(KBr): 2955, 2890, 1710, 1245, 1120, 1070 cm⁻¹.
UV: λmax 266 nm

EXAMPLE 20

Preparation of 5-fluoro-2′-deoxyuridine-5′-linolenylphosphate (Y=H, A=—(CH₂)₂CH≝CHCH₂CH≝CH CH₂CH≝CH(CH₂)₈—, R=H)

500 mg (0.794 mmole) of 3′-acetyl-5-fluoro-2′-deoxyuridine-5′-linolenylphosphate prepared in Example 19 was treated in the same way as Example 16 to obtain 365 mg of powdery 5-fluoro-2′-dexyuridine-5-linolenylphosphate. The yield was 78%.

IR(KBr): 3490, 2950, 2875, 1710, 1260, 1210, 1065 cm⁻¹.
UV: λmax 268 nm

EXAMPLE 21

Preparation of 3′-acetyl-5-fluoro-2′-deoxyuridine-5′-(3-tetradecynyl)-phosphate (Y=H, A=—(CH₂)₁₀C≡C (CH₂)₂—, R=—COCH₃)

0.65 g (2.2 mmole) of 3-tetradecynylphosphate and 0.54 g (1.9 mmole) of 3′-acetyl-5-fluorouridine were dissolved in 20 ml of anhydrous pyridine. 1.41 g (7.6 mmole) of p-toluenesufonyl chloride was added to the solution with stirring while cooling with ice and the mixture was stirred overnight at room temperature.

Thereafter, the reaction mixture was treated according to Example 9 to obtain 0.96 g of powdery 3′-acetyl-5-fluorouridine-5′-(3-tetradecynyl) phosphate. The yield was 87%

Melting point: 170°~175° C.
IR(KBr): 2950, 2880, 1710, 1242, 1115, 1070 cm⁻¹.
UV $\lambda_{max}^{MeOH}$ 267 nm

EXAMPLE 22

Preparation of 5-fluoro-2′-deoxyuridine-5′-(3-tetradecinyl)phosphate (Y=H, A=—(CH₂)₁₀C≡C (CH₂)₂—, R=H)

0.8 g (1.3 mmole) of 3′-acetyl-5-fluoro-2′-deoxyuridine-5′-(3-tetradecynyl)phosphate prepared in Example 21 was treated according to Example 16, wherein butanol was removed from the butanol solution under reduced pressure to obtain 0.65 g of powderly 5-fluoro-2′-deoxyuridine-5′-(3-tetradecynyl)phosphate. The yield was 91%.

Melting point: 107°~108.5° C.
IR(neat): 3500, 2950, 2860, 1710, 1260, 1210, 1060 cm⁻¹.
UV: λmax 267 nm
NMR($\delta_{CDCl_3-D_3OD}^{TMS}$): 0.88 (br.t, 3H), 1.0~1.7 (m, 16H), 1.8~2.8 (m, 6H), 3.8~4.7 (m, 6H), 6.28 (br.t, 1H), 7.86 (d, 1H, J=6.5 Hz)

EXAMPLE 23

Preparation of 3′-acetyl-5-fluoro-2′-deoxyuridine-5′-(3-phenylpropyl)-phosphate

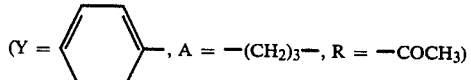

(Y = phenyl—, A = —(CH₂)₃—, R = —COCH₃)

1.30 g (6.0 mmole) of 3-phenylpropylphosphate and 1.15 g (4.0 mmole) of 3′-acetyl-5-fluoro-2′-dexyuridine were dissolved in 100 ml of anhydrous pyridine. 2.29 g (12.0 mmole) of p-toluenesulfonyl chloride was added thereto with stirring at room temperature and the mixture was stirred overnight.

The reaction mixture was then treated in the same way as Example 9 to obtain 1.14 g of powdery 3′-acetyl-5-fluoro-2′-deoxyuridine-5′-(3-phenylpropyl) phosphate. The yield was 59%.

IR(KBr): 3070, 3030, 2950, 1702, 1192, 1124, 1060 cm⁻¹.

UV: $\lambda_{max}^{MeOH}$ 267 nm

NMR($\delta_{CDCl_3}^{TMS}$) after CH$_2$N$_2$ treatment: 1.7~2.85 (m, 6H), 2.06 (s, 3H), 3.29 (s, 3H, N-Me), 3.72 (d, 3H, J=11 Hz), 3,8~4.6 (m, 5H) 5.1~5.35 (m, 1H), 6.25 (br.t, 1H), 7.12 (s, 5H), 7.68 (d, 1H, J=6 Hz)

EXAMPLE 24

Preparation of 5-fluoro-2'-deoxyuridine-5'-(3-phenylpropyl)phosphate

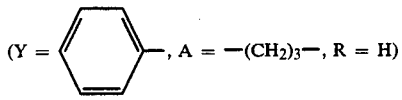
(Y = phenyl, A = —(CH$_2$)$_3$—, R = H)

600 mg (1.23 mmole) of 3'-acetyl-5-fluoro-2'-deoxyuridine-5'-(3-phenylpropyl)phosphate prepared in Example 23 was treated according to Example 16, wherein butanol was removed from the butanol solution under reduced pressure to obtain 479 mg of oily 5-fluoro-2'-deoxyuridine-5'-(3-phenylpropyl)phosphate. The yield was 87%.

IR(neat): 3490, 3050, 2990, 1710, 1602, 1500, 1472, 1452, 1405, 1358, 1264, 1124 cm$^{-1}$.

UV: $\lambda_{max}^{MeOH}$ 267 nm

NMR($\delta_{CDCl_3}^{TMS}$) after CH$_2$N$_2$ treatment: 1.7~2.85 (m, 6H), 3.29 (s, 3H, N-Me), 3.73 (d, 3H, J=11 Hz), 3.8~4.55 (m, 6H), 6.21 (br.6, 1H), 7.12 (s, 5H), 7.62 (d, 1H, J=6 Hz).

EXAMPLE 25

Preparation of 3'-acetyl-5-fluoro-2'-deoxyuridine-5'-(3-(p-chlorophenyl)propyl)phosphate

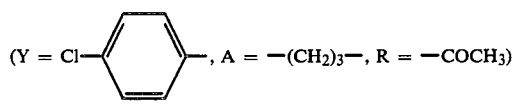
(Y = Cl—phenyl, A = —(CH$_2$)$_3$—, R = —COCH$_3$)

1.94 g (7.7 mmole) of 3-(p-chlorophenyl)propylphosphate and 1.48 g (5.2 mmole) of 3'-acetyl-5-fluorouridine were dissolved in 30 ml of anhydrous pyridine. 3.93 g (20.6 mmole) of p-toluenesulfonyl chloride was added to the solution with stirring while cooling with ice and the mixture was stirred overnight at room temperature. The mixture was again cooled with ice and 10 ml of water was added thereto and the mixture was stirred for 30 minutes. Thereafter, the reaction mixture was treated according to Example 9 to give 1.17 g of powdery 3'-acetyl-5-fluoro-2'-deoxyuridine-5'-(3-(p-chlorophenyl)propyl) phosphate. The yield was 44%.

IR(KBr): 3100, 2980, 1710, 1360, 1240, 1064 cm$^{-1}$.

UV: $\lambda$max 267 nm

NMR($\delta_{CDCl_3}^{TMS}$) after CH$_2$N$_2$ treatment: 1.75~2.85 (m, 6H), 2.06 (s, 3H), 3.31 (s, 3H, N-Me), 3.76 (d, 3H, J=11 Hz), 3.9~4.5 (m, 5H), 5.1~5.4 (m, 1H), 6.28 (br.t, 1H), 6.9~7.35 (m, 4H), 7.68 (d, 1H, J=6 Hz)

EXAMPLE 26

Preparation of 3'-acetyl-5-fluoro-2'-deoxyuridine-5'-(4-phenylbutyl)-phosphate

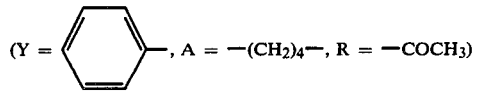
(Y = phenyl, A = —(CH$_2$)$_4$—, R = —COCH$_3$)

1.38 g (6.0 mmole) of 4-phenylbutylphosphate and 1.15 g (4.07 mmole) of 3'-acetyl-5-fluoro-2'-deoxyuridine were dissolved in 100 ml of anhydrous pyridine. 2.29 g (12.0 mmole) of p-toluenesulfonyl chloride was added to the solution with stirring at room temperature and the mixture was stirred overnight.

After that, the reaction mixture was treated according to Example 9 to give 1.48 g of powdery 3'-acetyl-5-fluoro-2'-deoxyuridine-5'-(4-phenylbutyl) phosphate. The yield was 74%.

IR(KBr): 3070, 3025, 2950, 1710, 1232, 1185, 1125, 1140 cm$^{-1}$.

UV: $\lambda_{max}^{MeOH}$ 267 nm

EXAMPLE 27

Preparation of 5-fluoro-2'-deoxyuridine-5'-(4-phenylbutyl)phosphate

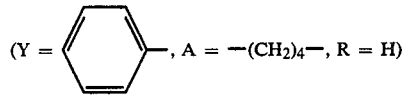
(Y = phenyl, A = —(CH$_2$)$_4$—, R = H)

940 mg 1.88 mmole) of 3'-acetyl-5-fluoro-2'-deoxyuridine-5'-(4-phenylbutyl)phosphate prepared in Example 26 was treated in the same way as Example 16, wherein butanol was removed from the butanol solution under reduced pressure to give 667 mg of oily 5-fluoro-2'-deoxyuridine-5'-(4-phenylbutyl) phosphate. The yield was 93%.

IR(KBr): 3480, 3100, 2975, 1710, 1268, 1128, 1136, 1010 cm$^{-1}$.

UV: $\lambda_{max}^{MeOH}$ 267 nm

NMR($\delta_{CDCl_3}^{TMS}$): 1.5~1.9 (m, 4H), 2.1~2.8 (m, 4H), 3.7~4.6 (m, 6H), 6.3 (br.s, 1H), 7.25 (s, 5H), 7.82 (d, 1H, J=7 Hz)

EXAMPLE 28

Preparation of 3'-acetyl-5-fluoro-2'-deoxyuridine-5'-(8-phenyloctyl)-phosphate

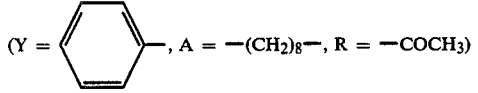
(Y = phenyl, A = —(CH$_2$)$_8$—, R = —COCH$_3$)

1.59 g (5.56 mmole) of 8-phenyloctylphosphate and 1.15 g (4.0 mmole) of 3'-acetyl-5-fluoro-2'-deoxyuridine were dissolved in 80 ml of anhydrous pyridine. 2.29 g (12.0 mmole) of p-toluenesulfonyl chloride was added thereto with stirring at room temperature and the mixture was stirred overnight.

Thereafter, the reaction mixture was treated according to Example 9, wherein butanol was removed from the butanol solution to obtain 1.03 g of oily 3'-acetyl-5-fluoro-2'-deoxyuridine-5'-(8-phenyloctyl) phosphate. The yield was 46%.

IR(neat): 3100, 3050, 2955, 2880, 1710, 1366, 1240, 1070 cm$^{-1}$.

UV: $\lambda_{max}^{MeOH}$ 267 nm

EXAMPLE 29

Preparation of 5-fluoro-2'-deoxyuridine-5'-(8-phenyloctyl)phosphate

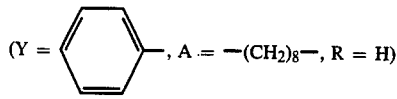

(Y = phenyl, A = —(CH$_2$)$_8$—, R = H)

515 mg (0.93 mmole) of 3'-acetyl-5-fluoro-2'-deoxyuridine-5'-(8-phenyloctyl)phosphate prepared in Example 28 was treated according to Example 16, wherein butanol was removed from the butanol solution under reduced pressure to give 445 mg of oily 5-fluoro-2'-deoxyuridine-5'-(8-phenyloctyl)phosphate. The yield was 94%.

IR(neat): 3490, 3100, 3045, 2975, 2950, 2875, 1708, 1265, 1208, 1070 cm$^{-1}$.

UV: $\lambda_{max}^{MeOH}$ 267 nm

EXAMPLE 30

Preparation of 3'-acetyl-5-fluoro-2'-deoxyuridine-5'-(8-phenyl-3-octynyl)phosphate

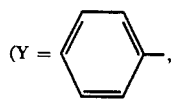

A = —(CH$_2$)$_4$C≡C(CH$_2$)$_2$—, R = —COCH$_3$ 1.80 g (6.38 mmole) of (8-phenyl-3-octynyl) phosphate and 1.31 g (4.56 mmole) of 3'-acetyl-5-fluoro-2'-deoxyuridine were dissolved in 90 ml of anhydrous pyridine. 2.61 g (13.7 mmole) of p-toluenesulfonyl chloride was added to the solution with stirring at room temperature and the mixture was stirred overnight.

Thereafter, the reaction mixture was treated according to Example 9, wherein butanol was removed from the butanol solution under reduced pressure to give 1.73 g of oily 3-acetyl-5-fluoro-2'-deoxyuridine-5'-(8-phenyl-3-octynyl)phosphate. The yield was 69%.

IR(neat): 3100, 3045, 2955, 2890, 1710, 1240, 1070 cm$^{-1}$.

UV: $\lambda_{max}^{MeOH}$ 267 nm

EXAMPLE 31

Preparation of 5-fluoro-2'-deoxyuridine-5'-(8-phenyl-3-octynyl)phosphate

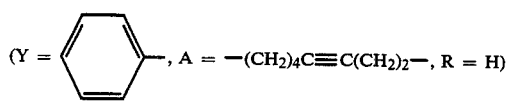

575 mg 1.04 mmole) of 3'-acetyl-5-fluoro-2'-deoxyuridine-5'-(8-phenyl-3-octynyl)phosphate prepared in Example 30 was treated according to Example 16, wherein butanol was removed from the butanol solution to obtain 424 mg of oily 5-fluoro-2'-deoxyuridine-5'-(8-phenyl-3-octynyl)phosphate. The yield was 82%.

IR(neat): 3490, 2950, 2860, 1718, 1692, 1660, 1268, 1208, 1132, 1070, 1040 cm$^{-1}$.

UV: $\lambda_{max}^{MeOH}$ 267 nm

EXAMPLE 32

Preparation of 3'-acetyl-5-fluoro-2'-deoxyuridine-5'-(o-chlorophenyl)-phosphate

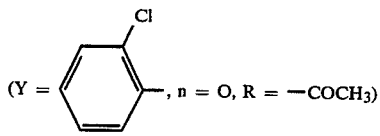

(Y = o-chlorophenyl, n = 0, R = —COCH$_3$)

1.44 g (7.0 mmole) of o-chlorophenylphosphate and 2.0 g (7.0 mmole) of 3'-acetyl-5-fluoro-2'-deoxyuridine were dissolved in 50 ml of anhydrous pyridine. 4.0 g (21.0 mmole) of p-toluenesulfonyl chloride was added to the solution with stirring at room temperature and the mixture was stirred overnight.

Thereafter, the reaction mixture was treated according to Example 9, wherein butanol was removed from the butanol solution under reduced pressure to obtain 1.5 g of 3'-acetyl-5-fluoro-2'-deoxyuridine-5'-(0-chlorophenyl)phosphate. The yield was 58%.

IR(KBr): 1710, 1480, 1240, 1100, 1060 cm$^{-1}$.

UV: $\lambda_{max}^{MeOH}$ 264 nm

EXAMPLE 33

Preparation of 3'-acetyl-5-fluoro-2'-deoxyuridine-5'-(p-octylphenyl)-phosphate

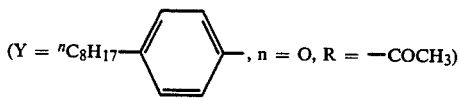

(Y = $^nC_8H_{17}$—, n = 0, R = —COCH$_3$)

858 mg (3.0 mmole) of p-octylphenylphosphate and 576 mg (2.0 mmole) of 3'-acetyl-5-fluoro-2'-deoxyuridine were dissolved in 40 ml of anhydrous pyridine. 1.18 g (6.2 mmole) of p-toluenesulfonyl chloride was added to the solution with stirring at room temperature and the mixture was stirred overnight.

Thereafter, the reaction mixture was treated in the same way as Example 9 to obtain 917 mg of powdery 3'-acetyl-5-fluoro-2'-deoxyuridine-5'-(p-octylphenyl)-phosphate. The yield was 82%.

IR(KBr): 3095, 2950, 2870, 1708, 1510, 1465, 1360, 1235, 1100, 1060 cm$^{-1}$.

UV: $\lambda_{max}^{MeOH}$ 267 nm

EXAMPLE 34

Preparation of 5-fluoro-2'-deoxyuridine-5'-(p-octylphenyl)phosphate

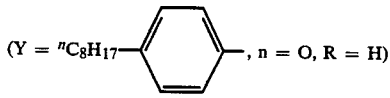

(Y = $^nC_8H_{17}$—, n = 0, R = H)

460 mg (0.83 mmole) of 3'-acetyl-5-fluoro-2'-deoxyuridine-5'-(p-octylphenyl)phosphate prepared in Example 33 was treated according to Example 16 to obtain 386 mg of powdery 5-fluoro-2'-deoxyuridine-5'-(p-octylphenyl)phosphate. The yield was 91%.

IR(KBr): 3400, 3055, 2950, 2880, 1720, 1698, 1665, 1505, 1465, 1262, 1238, 1204, 1025 cm$^{-1}$.

UV: $\lambda_{max}^{MeOH}$ 268 nm

EXAMPLE 35

Preparation of 3'-acetyl-5-fluoro-2'-deoxyuridine-5'-(3-(p-pentylphenyl)propyl)phosphate

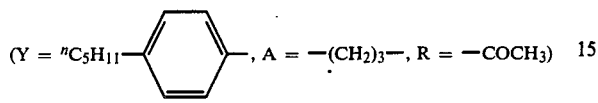

1.86 g (6.5 mmole) of 3-(p-pentylphenyl)propyl-phosphate and 1.44 g (5.0 mmole) of 3'-acetyl-5-fluoro-2'-deoxyuridine were dissolved in 75 ml of anhydrous pyridine. 2.86 g (15.0 mmole) of p-toluensulfonyl chloride was added to the solution with stirring at room temperature and the mixture was stirred overnight.

After that, the reaction mixture was treated in the same way as Example 9 to give 1.17 g powdery 3'-acetyl-5-fluoro-2'-deoxyuridine-5'-(3-(p-pentylphenyl) propyl)phosphate. The yield was 42%.

IR(KBr): 3100, 3025, 2975, 2950, 2865, 1710, 1512, 1464, 1360, 1230, 1110, 1060 cm$^{-1}$.

UV: $\lambda_{max}^{MeOH}$ 266 nm

EXAMPLE 36

Preparation of 5-fluoro-2'-deoxyuridine-5'-3-(p-penylphenyl)propyl)-phosphate

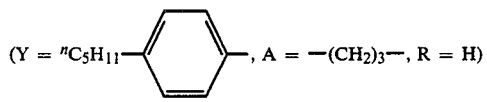

500 mg (0.90 mmole) of 3'-acetyl-5-fluoro-2'-deoxyuridine-5'-(3-(p-pentylphenyl)propyl)phosphate prepared in Example 35 was treated according to Example 16 to obtain 347 mg of powdery 5-fluoro-2'-deoxyuridine-5'-(3-(p-pentylphenyl)propyl)phosphate. The yield was 75%.

Melting point: 123°~125° C.

IR(KBr): 3480, 3095, 2950, 2865, 1710, 1260, 1210 cm$^{-1}$.

UV: $\lambda_{max}^{MeOH}$ 265 nm

NMR($\delta_{CDCl_3-D_3COD}^{TMS}$): 0.89 (br.t, 3H), 0.9~1.9 (m, 12H), 1.9~2.8 (m, 4H), 3.9~4.7 (m, 4H), 6.32 (br.t, 1H), 7.20 (s, 4H), 7.88 (d, 1H, J=6 Hz)

EXAMPLE 37

Preparation of 3'-acetyl-5-fluoro-2'-deoxyuridine-5'-(3-(p-pentanoylphenyl)propyl)phosphate

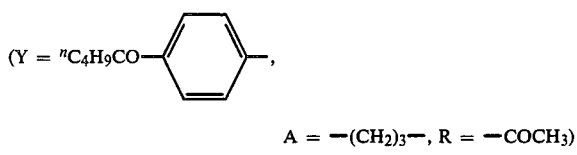

2.9 g (9.7 mmole) of 3-(p-pentanoylphenyl)propyl-phosphate and 1.85 g (6.4 mmole) of 3'-acetyl-5-fluoro-2'-deoxyuridine were dissolved in 50 ml of anhydrous pyridine. 3.67 g (19.2 mmole) of p-toluenesulfonyl chloride was added to the solution with stirring while cooling with ice and the mixture was stirred overnight at room temperature.

Thereafter, the reaction mixture was treated according to Example 9 to obtain 1.96 g of 3'-acetyl-5-fluoro-2'-deoxyuridine-5'-(3-(p-pentanoylphenyl) propyl)phosphate. The yield was 54%.

IR(KBr): 2990, 1710, 1410, 1364, 1212, 1036 cm$^{-1}$.

UV: $\lambda_{max}^{CH_3CN-H_2O}$ 257 nm

EXAMPLE 38

Preparation of 5-fluoro-2'-deoxyuridine-5'-(3-(p-pentanoylphenyl)-propyl)phosphate

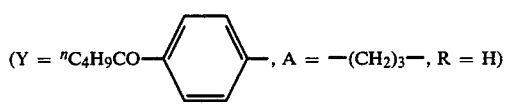

1.8 g (3.16 mmole) of 3'-acetyl-5-fluoro-2'-deoxyuridine-5'-(3-(p-pentanoylphenyl)propyl) phosphate prepared in Example 37 was treated according to Example 16, wherein butanol was removed from the butanol solution under reduced pressure to give 0.99 g of oily 5-fluoro-2'-deoxyuridine-5'-(3-(p-pentanoylphenyl)propyl) phosphate. The yield was 53%.

IR(neat): 2980, 2895, 1705, 1608, 1466, 1410, 1358, 1260 cm$^{-1}$.

UV: $\lambda_{max}^{CH_3CN-H_2O}$ 256 nm

EXAMPLE 39

Preparation of 3'-octanoyl-5-fluoro-2'-deoxyuridine-5'-decylphosphate (Y=H, A=—(CH$_2$)$_{10}$—, R=—CO$^n$C$_7$H$_{15}$)

432 mg (1.81 mmole) of decylphosphate and 450 mg (1.21 mmole) of 3'-octanoyl-5-fluoro-2'-deoxyuridine were dissolved in 30 ml of anhydrous pyridine. 950 mg (5.0 mmole) of p-toluenesulfonyl chloride was added to the solution with stirring at room temperature and the mixture was stirred overnight.

After that, the reaction mixture was treated according to Example 9 to obtain 538 mg of powdery 3'-octanoyl-5-fluoro-2'-deoxyuridine-5'-decyl phosphate. The yield was 75%.

IR(KBr): 2945, 2865, 1710, 1464, 1358, 1250, 1220, 1110, 1065 cm$^{-1}$.

UV: $\lambda_{max}^{MeOH}$ 267 nm

EXAMPLE 40

Preparation of 3'-butanoyl-5-fluoro-2'-deoxyuridine-5'-dodecylphosphate (Y=H, A=—(CH$_2$)$_{12}$—, R=CO$^n$C$_3$H$_7$)

860 mg (3.23 mmole) of dodecylphosphate and 680 mg (2.15 mmole) of 3'-butanoyl-5-fluoro-2'-deoxyuridine were dissolved in 30 ml of anhydrous pyridine. 1.23 g (6.45 mmole) of p-toluenesulfonyl chlorid was added to the solution with stirring at room temperature and the mixture was stirred overnight.

After that, the reaction mixture was treated according to Example 9 to give 689 mg of powdery 3'-butanoyl-5-fluoro-2'-deoxyuridine-5'-dodecylphosphate. The yield was 57%.

IR(KBr): 2950, 2865, 1710, 1468, 1358, 1250, 1100, 1064 cm$^{-1}$.

UV: $\lambda_{max}^{MeOH}$ 267 nm

EXAMPLE 41

Preparation of 3′-octanoyl-5-fluoro-2′-deoxyuridine-5′-octylphosphate (Y=H, A=—(CH$_2$)$_8$—, R=CO$^n$C$_7$H$_{15}$)

398 mg (1.89 mmole) of octylphosphate and 470 mg (1.26 mmole) of 3′-octanoyl-5-fluoro-2′-deoxyuridine were dissolved in 30 ml of anhydrous pyridine. 720 mg (3.78 mmole) of p-toluenesulfonyl chloride was added to the solution with stirring at room temperature and the mixture was stirred overnight.

Thereafter, the reaction mixture was treated in the same way as Example 9 to obtain 570 mg of oily 3′-octanoyl-5-fluoro-2′-deoxyuridine-5′-octylphosphate. The yield was 80%.

IR(neat): 2950, 2870, 1710, 1465, 1360, 1250, 1110, 1065 cm$^{-1}$.

UV: $\lambda_{max}^{MeOH}$ 267 nm

EXAMPLE 42

Preparation of 3′-acetyl-5-fluoro-2′-deoxyuridine-5′-undecylphosphate (Y=H, A=—(CH$_2$)$_{11}$—, R=—COCH$_3$)

2.27 g (9.0 mmole) of undecylphosphate and 1.73 g (6.0 mmole) of 3′-acetyl-5-fluoro-2′-deoxyuridine were dissolved in 160 ml of anhydrous pyridine. 3.44 g (18.0 mmole) of p-toluenesulfonyl chloride was added to the solution with stirring at room temperature and the mixture was stirred overnight.

Thereafter, the reaction mixture was treated in the same way as Example 9 to obtain 2.24 g of white powdery 3′-acetyl-5-fluoro-2′-deoxyuridine-5′-undecylphosphate. The yield was 71%.

IR(KBr): 2940, 2860, 1710, 1240, 1198, 1115, 1065 cm$^{-1}$.

UV: $\lambda_{max}^{MeOH}$ 267 nm

NMR($\delta_{CDCl_3}^{TMS}$) after CH$_2$N$_2$ treatment: 0.89 (br.t, 3H), 1.0~2.0 (m, 18H), 2.04 (s, 3H), 2.0~2.5 (m, 2H), 3.30 (s, 3H), 3.75 (d, 3H, J=11 Hz), 3.8~4.4 (m, 5H), 5.1~5.35 (m, 1H), 6.28 (br.t, 1H), 7.68 (d, 1H, J=6 Hz)

EXAMPLE 43

Preparation of 3′-acetyl-5-fluoro-2′-deoxyuridine-5′-heptadecylphosphate (Y=H, A=—(CH$_2$)$_{17}$—, R=—COCH$_3$)

1.52 g (3.0 mmole) of n-heptadecylphosphate and 0.86 g (3.0 mmole) of 3′-acetyl-5-fluoro-2′-deoxyuridine were dissolved in 80 ml of anhydrous pyridine. 1.72 g (9.0 mmole) of p-toluenesulfonyl chloride was added thereto with stirring at room temperature and the mixture was stirred overnight.

Thereafter, the reaction mixture was treated in the same way as Example 9 to obtain 1.25 g of white powdery 3′-acetyl-5-fluoro-2′-deoxyuridine-5′-heptadecylphosphate. The yield was 69%.

IR(KBr): 2940, 2860, 1710, 1240, 1198, 1110, 1062 cm$^{-1}$.

UV: $\lambda_{max}^{MeOH}$ 267 nm

NMR($\delta_{CDCl_3}^{TMS}$) after CH$_2$N$_2$ treatment: 0.88 (br.t, 3H), 1.0~2.0 (m, 30H), 2.06 (s, 3H), 2.0~2.5 (m, 2H), 3.31 (s, 3H), 3.76 (d, 3H, J=11 Hz), 3.8~4.4 (m, 5H), 5.1~5.35 (m, 1H), 6.28 (br.t, 1H), 7.69 (d, 1H, J=6 Hz)

EXAMPLE 44

Preparation of 5-fluoro-2′-deoxyuridine-5′-heptadecylphosphate (Y=H, A=—(CH$_2$)$_{17}$—, R=H)

701 mg (1.16 mmole) of 3′-acetyl-5-fluoro-2′-deoxyuridine-5′-heptadecylphosphate prepared in Example 43 was treated in the same way as Example 16 to obtain 519 mg of white powdery 5-fluoro-2′-deoxyuridine-5′-heptadecylphosphate. The yield was 9%.

Melting point: 132°~133.5° C.

IR(KBr): 3490, 2940, 2860, 1718, 1690, 1658, 1262, 1220, 1130, 1065, 1040 cm$^{-1}$.

UV: $\lambda_{max}^{MeOH}$ 267 nm NMR($\delta_{CDCl_3-D_3COD}^{TMS}$): 0.88 (br.t, 3H), 1.0~1.9 (m, 30H), 2.0~2.5 (m, 2H), 3.8~4.6 (m, 6H), 6.28 (br.t, 1H), 7.89 (d, 1H, J=6.5 Hz)

EXAMPLE 45

Preparation of 3′-benzoyl-5-fluoro-2′-deoxyuridine-5′-tetradecylphosphate

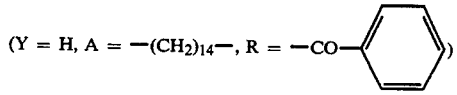

(Y = H, A = —(CH$_2$)$_{14}$—, R = —CO—⟨phenyl⟩)

1.16 g (3.75 mmole) of tetradecylphosphate and 0.88 g (2.5 mmole) of 3′-benzoyl-5-fluoro-2′-deoxyuridine were dissolved in 80 ml of anhydrous pyridine. 1.43 g (7.5 mmole) of p-toluenesulfonyl chloride was added to the solution with stirring at room temperature and the mixture was stirred overnight.

The reaction mixture was thereafter treated according to Example 9 to obtain 799 mg of 3′-benzoyl-5-fluoro-2′-deoxyuridine-5′-tetradecylphosphate. The yield was 50%.

IR(KBr): 2940, 2860, 1718, 1262, 1210, 1105, 1065 cm$^{-1}$.

UV: $\lambda_{max}^{MeOH}$ 267 nm

EXAMPLE 46

Efficacy against solid tumor

A series of experiments were conducted with the use of groups of five ICR mice (7 weeks old, male, weighing about 30 g) by transplanting 3×10$^6$ Sarcoma 180 tumor cells to the inguinal region of each mouse subcutaneously. The compounds prepared in the aforementioned Examples were administered orally 1, 3, and 5 days, after the transplantation of tumor cells. As 5-FU, a control drug in the experiment, is known not to display much effect when administered orally, it was administered intraperitoneally. The weight of tumor was measured 10 days after the transplantation and the antitumor activity was expressed by the ratio (%) of thus measured weight to the weight of tumor of the mice belonging to the control groups in which the mice were administered with only a phosphate buffered saline solution (PBS) containing no drug.

The results are shown in Table 1

TABLE 1

| Compound | Dose (mg/kg) | T/C (%) | Judgment |
| --- | --- | --- | --- |
| Compound of Example 1 | 20 | 33 | ++ |
|  | 10 | 43 |  |
|  | 5 | 53 |  |
|  | 2.5 | 57 |  |
| Compound of | 100 | 57 | + |

TABLE 1-continued

| Compound | Dose (mg/kg) | T/C (%) | Judgment |
|---|---|---|---|
| Example 2 | 50 | 65 | |
| | 25 | 83 | |
| Compound of | 200 | 30 | ++ |
| Example 3 | 100 | 49 | |
| | 50 | 65 | |
| Compound of | 200 | 55 | ++ |
| Example 4 | 100 | 64 | |
| | 50 | 56 | |
| | 25 | 39 | |
| Compound of | 200 | 2 | +++ |
| Example 6 | 100 | 11 | |
| | 50 | 15 | |
| | 25 | 45 | |
| | 12 | 46 | |
| | 6 | 76 | |
| Compound of | 200 | 39 | ++ |
| Example 7 | 100 | 39 | |
| | 50 | 42 | |
| | 25 | 67 | |
| Compound of | 200 | 38 | ++ |
| Example 8 | 100 | 42 | |
| | 50 | 75 | |
| | 25 | 55 | |
| Compound of | 200 | 47 | ++ |
| Example 10 | 100 | 39 | |
| | 50 | 32 | |
| | 25 | 51 | |
| Compound of | 200 | 18 | +++ |
| Example 11 | 100 | 34 | |
| | 50 | 14 | |
| | 25 | 32 | |
| | 12 | 40 | |
| | 6 | 46 | |
| | 3 | 39 | |
| | 1.5 | 39 | |
| Compound of | 100 | 15 | +++ |
| Example 12 | 25 | 27 | |
| | 12 | 37 | |
| Compound of | 200 | 6 | +++ |
| Example 13 | 100 | 31 | |
| | 50 | 10 | |
| | 25 | 22 | |
| | 12 | 35 | |
| | 6 | 64 | |
| Compound of | 200 | 9 | +++ |
| Example 14 | 100 | 20 | |
| | 50 | 22 | |
| | 25 | 19 | |
| Compound of | 200 | 6 | +++ |
| Example 15 | 50 | 20 | |
| | 12 | 41 | |
| Compound of | 200 | 25 | ++ |
| Example 17 | 50 | 22 | |
| | 12 | 30 | |
| Compound of | 200 | 35 | ++ |
| Example 18 | 50 | 30 | |
| | 12 | 36 | |
| Compound of | 200 | 36 | ++ |
| Example 19 | 50 | 44 | |
| | 12 | 46 | |
| Compound of | 200 | 30 | ++ |
| Example 20 | 50 | 32 | |
| | 12 | 41 | |
| Compound of | 100 | 44 | ++ |
| Example 23 | 25 | 48 | |
| | 6 | 57 | |
| Compound of | 200 | 26 | ++ |
| Example 24 | 100 | 82 | |
| | 25 | 81 | |
| | 6 | 90 | |
| Compound of | 100 | 36 | ++ |
| Example 26 | 25 | 46 | |
| | 6 | 54 | |
| Compound of | 200 | 53 | + |
| Example 27 | 100 | 54 | |
| | 25 | 54 | |
| | 6 | 88 | |
| Compound of | 200 | 60 | ++ |
| Example 32 | 50 | 69 | |
| | 12 | 47 | |
| Compound of | 200 | 28 | ++ |
| Example 33 | 50 | 41 | |
| | 12 | 33 | |
| Compound of | 200 | 40 | ++ |
| Example 34 | 50 | 85 | |
| | 12 | 100 | |
| Compound of | 200 | 60 | + |
| Example 35 | 50 | 70 | |
| | 12 | 66 | |
| Compound of | 200 | 40 | ++ |
| Example 36 | 50 | 60 | |
| | 12 | 64 | |
| Compound of | 200 | 30 | ++ |
| Example 37 | 50 | 60 | |
| | 12 | 62 | |
| Compound of | 200 | 65 | + |
| Example 38 | 50 | 88 | |
| | 12 | 71 | |
| Compound of | 200 | 36 | ++ |
| Example 39 | 50 | 40 | |
| | 12 | 47 | |
| Compound of | 200 | 14 | +++ |
| Example 40 | 50 | 31 | |
| | 12 | 78 | |
| Compound of | 200 | 21 | ++ |
| Example 41 | 50 | 30 | |
| | 12 | 48 | |
| Compound of | 200 | 35 | ++ |
| Example 42 | 50 | 60 | |
| | 12 | 69 | |
| Compound of | 200 | 38 | ++ |
| Example 44 | 50 | 69 | |
| | 12 | 83 | |
| 5-FU (Positive control) | 20 | 68 | + |
| | 5 | 77 | |

The results of evaluation of the antitumor activity are expressed by:
(+) fairly effective for T/C 70~51.
(++) effective for T/C 50~21.
(+++) very effective for T/C 20 or less.
(See "Applied Pharmacology" 7, pp. 1277~1279, 1973)

EXAMPLE 47

Efficacy against ascites tumor $1 \times 10^5$ mouse leukemic cells L1210 were transplanted intra-peritoneally to group of five $CDF_1$ mice (male, 8 weeks old, weighing about 27 g). The test compounds prepared in the aforementioned Examples were administered orally three times, i.e., 1, 3, and 5 days after the transplantation respectively. The antitumor activity was expressed by the increase of life span (ILS %) as compared with the mice of the control groups which were administered only with a phosphate buffered saline solution which was used in making a suspension of aforementioned test compound. The results are shown in Table 2. The result obtained with 5-FUdR is also shown in the table.

TABLE 2

| Compound | Dose (mg/kg) | ILS (%)* |
|---|---|---|
| Compound of | 40 | 20 |
| Example 4 | 20 | 12 |
| | 10 | 12 |
| | 5 | 12 |
| Compound of | 200 | 15 |
| Example 2 | 100 | 20 |
| | 40 | 22 |
| | 20 | 22 |
| | 10 | 12 |
| | 5 | 10 |
| | 2.5 | 7 |
| Compound of | 50 | Toxic |
| Example 1 | 20 | 60 |
| | 10 | 43 |
| | 5 | 33 |
| | 2.5 | 25 |

TABLE 2-continued

| Compound | Dose (mg/kg) | ILS (%)* |
|---|---|---|
| Compound of | 400 | 35 |
| Example 11 | 100 | 52 |
| | 50 | 21 |
| | 25 | 17 |
| | 12 | 20 |
| | 6 | 10 |
| 5-FUdR | 40 | 10 |
| (Positive control) | 20 | 12 |
| HCFU** | 200 | 28 |
| (Positive control) | 50 | 0 |
| | 12 | 0 |

Notes:
*(1)The larger the value is, the greater the effect is.
**(2)1-hexylcarbamoyl-5-fluorouridine $$^{(3)}ILS\ (\%) = \frac{\text{Average life span (days) obtained with groups administered with compound}}{\text{Average life span (days) obtained with control groups}} \times 100 - 100$$

(4)As shown in Table 2, the compound of Example 11 of the present invention showed the activity in the smaller administration as compared with HCFU.

EXAMPLE 48

Antitumor effect against mouse mammary carcinoma

Groups of five C3H mice were subjected to the experiment in which $4 \times 10^6$ mammary carcinoma MM46 cells syngeneic to C3H mouse were administered subcutaneously to the inguinal region of each mouse. Drugs were administered orally six times, i.e., 1, 3, 5, 9, and 11 days after the transplantation.

The mice were sacrified 14 days after the transplantation and the tumor weight was measured. The antitumor effect was assessed by a percentage of the weight thus measured to the weight obtained from the control groups as follows:

$$T/C\ (\%) = \frac{\text{Weight of tumor obtained from groups administered with test compound}}{\text{Weight of tumor obtained from control groups}} \times 100$$

The results are shown in Table 3.

TABLE 3

| | Dose (mg/kg) | T/C (%) |
|---|---|---|
| Control group | — | 100 |
| Compound of | 100 | 38 |
| Example 11 | 50 | 60 |
| | 25 | 80 |
| HCFU | 100 | 50 |
| (Positive control) | 50 | 65 |
| | 25 | 70 |

The compound of Example 11 of the present invention showed the activity against mouse mammary carcinoma MM46 equal to or better than HCFU.

EXAMPLE 49

Antitumor effect against primary tumor and metastasis of Lewis' lung carcinoma

Groups of five C57BL/6 mice were subjected to the experiment in which $1.5 \times 10^5$ Lewis' lung carcinoma cells syngeneic to C57BL/mouse were transplanted to the footpad of each mouse. The Drugs were orally administered five times, i.e., 1, 3, 5, 7, and 9 days after the transplantation. The tumor was amputated from the transplanted region 12 days after the transplantation and the weight was measured. The antitumor effect against the primary tumor was evaluated by a percentage of the weight thus measured to the weight obtained from the control groups in the same way as Example 48.

Furthermore, the number of metastasis in the lung was counted 21 days after the transplantation. The inhibiting effect against metastasis was determined by a percentage of the number thus obtained to the number obtained from the control groups. The results are shown in Table 4.

TABLE 4

| | Dose (mg/kg) | Effect against primary tumor (%) | Effect against metastasis (%) |
|---|---|---|---|
| Control groups | — | 100 | 100 |
| Compound of | 100 | 38 | 6 |
| Example 11 | 50 | 54 | 23 |
| | 25 | 104 | 34 |
| | 12 | 90 | 29 |
| | 6 | 113 | 26 |

The effect against primary tumor was shown when the dosage was 50 mg/kg or more and the inhibiting effect against the metastasis was shown when the dosage was 6 mg/kg or more.

What we claim is:

1. 5-fluoro-2'-deoxyuridine derivatives expressed by general formula (1) and their pharmacologically permissible salts wherein A indicates a saturated or unsaturated divalent aliphatic hydrocarbon group having 1 to 30 carbon atoms; n indicates 0 or 1, and when n is 0, it indicated that Y is directly bound to an oxygen atom; Y represents a hydrogen atom, phenyl group, halogen-substituted phenyl group, alkyl-substituted phenyl group having 1 to 8 carbon atoms in the alkyl group, or an acyl substituted phenyl group having 1 to 8 carbon atoms in the acyl group; however, when Y is a hydrogen atom, n is 1; R indicates hydrogen atom or alcohol-protecting group, and wherein, when Y in general formula (1) is a hydrogen atom, A is a member selected from saturated or unsaturated divalent aliphatic hydrocarbon groups having 8 to 24 carbon atoms.

2. 5-Fluoro-2'-deoxyuridine derivatives according to claim 1, wherein, when Y in general formula (1) is a phenyl group, halogen-substituted phenyl group, alkyl-substituted phenyl group having 1 to 8 carbon atoms in the alkyl group, or an acyl-substituted phenyl group having 1 to 8 carbon atoms in the acyl group, A is a member selected from saturated or unsaturated divalent aliphatic hydrocarbon groups haveng 3 to 8 carbon atoms.

3. 5-Fluoro-2'-deoxyuridine derivatives according to claim 1, wherein, when Y in general formula (1) is a phenyl group, halogen-substituted phenyl group, alkyl-substituted phenyl group having 1 to 8 carbon atoms in the alkyl group, or an acyl-substituted phenyl group having 1 to 8 carbon atoms in the acyl group, n is 0.

4. 5-Fluoro-2'-deoxyuridine derivatives according to claim 1, wherein R in general formula (1) is a member selected from the group consisting of a hydrogen atom and acyl group having 1 to 10 carbon atoms.

5. An anti-tumor agent comprising a pharmaceutically acceptable carrier and a composition having anti-tumor activity on tumors transplanted into test animals comprising an anti-tumor effective amount of one or more 5-fluoro-2'-deoxyuridine derivatives expressed by the general formula (1) and their pharmacologically permissible salts

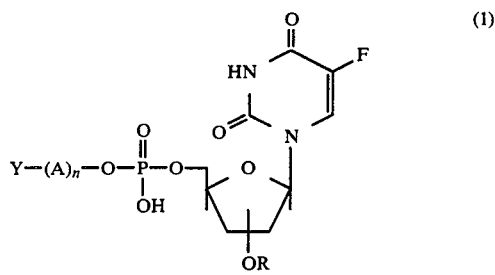

(1)

wherein A indicates a saturated or unsaturated divalent aliphatic hydrocarbon group having 1 to 30 carbon atoms; n indicates 0 or 1, and when n is 0, it indicates that Y is directly bound to an oxygen atom; Y represents a hydrogen atom, phenyl group, halogen-substituted phenyl group, alkyl-substituted phenyl group having 1 to 8 carbon atoms in the alkyl group, or an acyl substituted phenyl group having 1 to 8 carbon atoms in the acyl group; however when Y is a hydrogen atom, n is 1; R indicates hydrogen atom or alcohol-protecting group, and wherein, when Y in general formula (1) is a hydrogen atom, A is a member selected from saturated or unsaturated divalent aliphatic hydrocarbon groups having 8 to 24 carbon atoms.

6. An anti-tumor agent according to claim 5, wherein, when Y in general formula (1) is a phenyl group halogen-substituted phenyl group, alkyl-substituted phenyl group having 1 to 8 carbon atoms in the alkyl group, or an acyl-substituted phenyl group having 1 to 8 carbon atoms in the acyl group, A is a member selected from saturated or unsaturated divalent aliphatic hydrocarbon groups having 3 to 8 carbon atoms.

7. An anti-tumor agent according to claim 5, wherein, when Y in general formula (1) is a phenyl group, halogen-substituted phenyl group, alkyl-substituted phenyl group having 1 to 8 carbon atoms in the alkyl group, or an acyl-substituted phenyl group having 1 to 8 carbon atoms in the acyl group, n is 0.

8. A method of anti-tumor therapy comprising the use of a composition having anti-tumor activity on tumors transplanted into test animals comprising an anti-tumor effective amount of 5-fluoro-2'-deoxyuridine derivatives expressed by the general formula (1) and their pharmacologically permissible salts

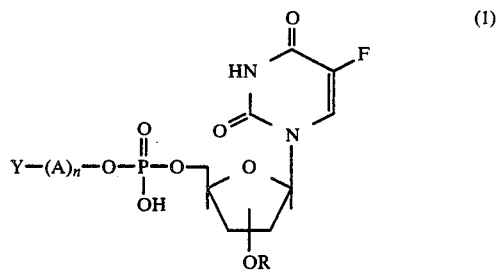

(1)

wherein A indicates a saturated or unsaturated divalent aliphatic hydrocarbon group having 1 to 30 carbon atoms; n indicates 0 or 1, and when n is 0, it indicates that Y is directly bound to an oxygen atom; Y represents a hydrogen atom, phenyl group, or substituted phenyl group; however, when Y is a hydrogen atom, n is 1; R indicates hydrogen atom or alcohol-protecting group, and wherein, when Y in general formula (1) is a hydrogen atom, A is a member selected from saturated or unsaturated divalent aliphatic hydrocarbon groups having 8 to 24 carbon atoms.

9. A method of antitumor therapy according to claim 8, wherein, when Y in general formula (1) is a phenyl group or substituted phenyl group, A is a member selected from saturated or unsaturated divalent aliphatic hydrocarbon groups having 3 to 8 carbon atoms.

10. A method of antitumor therapy according to claim 8, wherein, when Y in general formula (1) is a phenyl group or substituted phenyl group, n is 0.

* * * * *